United States Patent [19]

Möller et al.

[11] Patent Number: 4,959,478
[45] Date of Patent: Sep. 25, 1990

[54] METHOD OF PRODUCING-COARSE CRYSTALLINE NICOTINIC ACID WITH A HIGH DEGREE OF PURITY

[75] Inventors: Alexander Möller, Gelnhausen; Heinz Friedrich, Hanau; Herbert Kuhn, Alzenau; Kurt Winkler, Rossbach, all of Fed. Rep. of Germany

[73] Assignee: Degussa Aktiengesellschaft, Frankfurt am Main, Fed. Rep. of Germany

[21] Appl. No.: 318,414

[22] Filed: Feb. 28, 1989

Related U.S. Application Data

[63] Continuation of Ser. No. 41,004, Apr. 21, 1987, abandoned.

[30] Foreign Application Priority Data

Apr. 25, 1986 [DE] Fed. Rep. of Germany ....... 3614019

[51] Int. Cl.$^5$ ................ C07D 213/80; C07D 213/803
[52] U.S. Cl. .................................... 546/319; 546/318
[58] Field of Search ........................................ 546/319

[56] References Cited

U.S. PATENT DOCUMENTS 4,001,257  1/1977  Masuda ............................ 546/320

FOREIGN PATENT DOCUMENTS 2046556  4/1971  Fed. Rep. of Germany ...... 546/320
2438263  4/1975  Fed. Rep. of Germany ...... 546/319
2423755 10/1975  Fed. Rep. of Germany ...... 546/319

OTHER PUBLICATIONS

Chemical Abstracts 65, 5446a (1966), Abstract of Polish Patent 50,077.
J. E. Paustian, Chemtech, Mar. 1981, pp. 174–178.
J. A. Arkhipova et al, Zurnal Prikl, Khim. 35(2), 366–369 (1962).
B. V. Sovorov et al., Zurnal Prikl, Khim. 45, 2716–2718 (1972).
Ullmann, Encyklopadie der technischen Chemie, 4th Ed., vol. 23, p. 709.
Chem. Abst., vol. 65, p. 5446 (1966).

Primary Examiner—Alan L. Rotman
Attorney, Agent, or Firm—Cushman, Darby & Cushman

[57] ABSTRACT

The invention is directed to a method of producing coarse-crystalline nicotinic acid with a high degree of purity in which 3-cyanopyridine is saponified with aqueous alkali hydroxide and the nicotinic acid is allowed to crystallize out of the alkali nicotinate solution obtained in this manner under the addition of mineral acid at temperatures between 99° and 135° C. The pH is kept above 3.7.

7 Claims, 1 Drawing Sheet

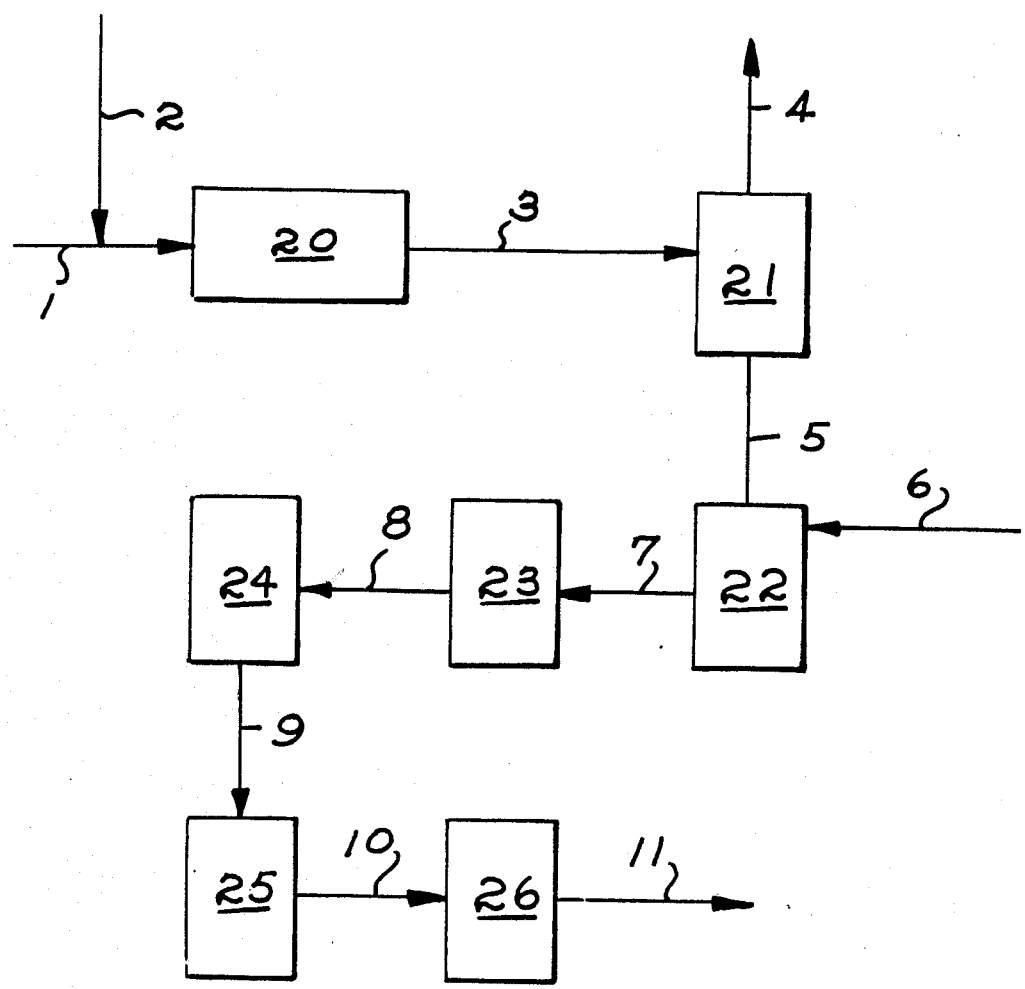

METHOD OF PRODUCING-COARSE CRYSTALLINE NICOTINIC ACID WITH A HIGH DEGREE OF PURITY

This is a continuation of application Ser. No. 041,004, filed Apr. 21, 1987, which was abandoned upon the filing hereof.

BACKGROUND OF THE INVENTION

The instant invention is directed to a method of producing coarse-crystalline nicotinic acid with a high degree of purity which is precipitated from alkaline alkali nicotinate solutions by the addition of mineral acid.

Many methods of producing nicotinic acid are known.

It can be obtained by liquid phase oxidation of alkyl pyridines (German Pat. No. 2,046,556; Masuda U.S. Pat. No. 4,001,257) acid hydrolysis of 3-cyanopyridine (German Pat. No. 2,438,263) or saponification of 3-cyanopyridine with ammonia and subsequent decomposition of the ammonium nicotinate by water vapor distillation. The use of sodium hydroxide solution for this purpose is known (C.A. 65, 5446 a 1966; Polish Pat. No. 50,077); however, the authors of this patent consider ammonia to be more suitable.

German Pat. No. 828,246 is also directed to the saponification of 3-cyanopyridine. According to this patent, the 3-cyanopyridine is caused to react with an excess of barium hydroxide, then the barium is precipitated with sulfuric acid and a raw nicotinic acid is separated out which must still be purified.

The low selectivity has up to now prevented an industrial realization of the catalytic gas phase reaction.

The methods which obtain nicotinic acid by the ammoniacal saponification of 3-cyanopyridine have the disadvantage that the nicotinic acid amide (nicotinamide) byproduct which accumulates here reduces the selectivity and the yield and, in addition, long reaction times are necessary (J. E. Paustian et al. Chemtech, Mar. 1981, 176 FIG. 4; J. A. Arkhipova et al. Zurnal Prikl, Khim. 35 (2), 366–369, 1962; B. V. Sovorov et al. Zurnal Prikl, Khim. 45, 2716–2718 (1972). Due to the strong tendency to sublimation of the nicotinic acid, the thermal decomposition of ammonium nicotinate by water vapor results in operational problems as a consequence of cloggings which can only be minimized by expensive apparatuses (German Pat. No. 2,423,755).

A disadvantage of all the methods described above is the fact that a nicotinic acid is obtained which does not meet the qualitative requirements for pharmaceuticals and foods until after additional purifying measures (Ullmann, Encyklopadie der technischen Chemie, 4th edition. volume 23, page 709 (1983).

In addition, the product accumulates in a finely crystalline form and is very dusty. The particle size distribution extends from $5\mu$ to $150\mu$. Since nicotinic acid is very irritating to the skin (Kirk-Othmer, Encyclopedia of Chemical Technology, volume 24, 3d edition, page 86), this can cause hygienic problems in the work area both for the manufacturer and also during further processing.

One tries to avoid this problem by granulating the finely crystalline nicotinic acid and thus obtaining a product with a particle spectrum between 100 and $315\mu$ (min. 90%) (Lonza Revue 1/85, 14015).

The invention has the task of creating a method which makes it possible to produce coarse-crystalline nicotinic acid suitable for pharmaceuticals and foods without granulation and purification steps by means of the saponification of 3-cyanopyridine with alkali hydroxide and subsequent precipitation of nicotinic acid with high yields.

SUMMARY OF THE INVENTION

The invention has as its object a method of producing coarse-crystalline nicotinic acid with a high degree of purity in which 3-cyanopyridine is saponified with alkali hydroxide and the nicotinic acid is subsequently obtained from the nicotinate formed, characterized in that an aqueous solution of 3-cyanopyridine is caused to react with equimolar amounts of an alkali hydroxide dissolved in water at temperatures between 130° and 190° C. and pressures between 1.5 and 2.0 MPa with 4 to 20 minutes, preferably 7 to 15 minutes, in a pressure reactor, e.g. a flow tube, the ammonia released during the reaction is separated according to known methods, e.g. by stripping, the ammonia-free alkali nicotinate solution is slowly treated at temperatures between 99° and 135° C., preferably 110° C., optionally under a pressure of 0.1–0.4 MPa, if the temperature is over the boiling point of the solution, with an aqueous mineral acid in such a manner that the pH of the solution remains above 3.7, the nicotinic acid suspension formed is subsequently cooled down to 0° to 20° C. and the crystallized nicotinic acid is separated out, e.g. by centrifuging, washed, dried and classified, if necessary. The method of the invention can be either continuous or discontinuous.

A product is obtained which is dust-free and of pharmaceutical quality (Europ. Arzneimittelbuch, Volume III, page 164 (1978).

The particle distribution is a function of the precipitation temperature and of the speed of addition of the mineral acid to the nicotinate solution.

The desired particle spectrum between 150 and $300\mu$ ($>75\%$) is reached if the mineral acid is added continuously within 2 to 4 hours, preferably 2.5 to 3.5 hours.

Hydrochloric acid and sulfuric acid are especially suitable as the acid, hydrochloric acid in a concentration of 10 to 25% by weight, preferably 15% by weight and sulfuric acid in a concentration of 15 to 25% by weight, preferably 20% by weight.

The mineral acids must be added only in such an amount that the pH of the solution does not get as low as 3.7.

A pH of 3.9 to 4.1, especially pH=4.0, is particularly suitable.

This fact is surprising to one skilled in the art, since, according to basic knowledge, ampholytes, which include pyridinecarboxylic acids, exhibit the lowest solubility at the isoelectric point This is stated for nicotinic acid to be pH=3.42 (Beilstein, monocarboxylic acids $CnH_{2n-7}$, $NO_2$ with one nitrogen atom, E III/IV 22, page 350 (1979).

Sodium hydroxide and potassium hydroxide in the form of 10 to 40% by weight aqueous solutions are especially suitable as alkali hydroxides.

3-cyanopyridine is added in the form of aqueous solutions with a content of 10 to 50% by weight 3-cyanopyridine.

The two reactants are preferably mixed with one another before being fed into the hydrolysis reactor.

The nicotinate solution being produced then accumulates in the corresponding dilution dependent on the initial solutions.

However, it can also be concentrated, especially to 30 to 60% by weight, by known measures prior to the precipitation of the nicotinic acid.

BRIEF DESCRIPTION OF THE DRAWINGS

The single FIGURE of the drawings diagrammatically illustrates the method of the invention.

DETAILED DESCRIPTION

As can be seen in the drawing, the process is carried out as follows:

An aqueous 3-cyanopyridine solution is pumped via line, 1, after an admixture of alkali hydroxide (line 2), into heated hydrolysis reactor 20. The reaction mixture passes via line 3 into stripper 21. The ammonia-water vapor mixture escapes via line 4 and is fed to an ammonia recovery. The ammonia-free alkali nicotinate solution passes via line 5 into precipitation reactor 22, which is loaded at the same time via line 6 with aqueous mineral acid. After the precipitation, the nicotinic acid suspension is taken off via line 7 and the crystallization is continued in crystallizer 23. Centrifuge 24 is loaded via line 8 for dewatering. Then, the filter cake passes via line 9 into drier 25. After classifying 26, the nicotinic acid is obtained via line 11. The oversize material is ground and the undersize material is recycled.

The process can comprise, consist essentially of or consist of the stated steps with the recited materials.

The invention is described further in the following examples.

EXAMPLE 1

10 kg of a 30% aqueous 3-cyanopyridine solution to which 3.85 kg of a 30% sodium hydroxide solution are mixed in hourly is fed hourly into a flow tube heated to 180° C.

After a dwell time of 10 minutes at a pressure of 2.0 MPa, the reaction solution is released to normal pressure and the ammonia produced is separated out with the help of a thin-layer evaporator. The nicotinic acid is precipitated from the ammonia-free sodium nicotinate solution obtained in this manner with 3 hours at 110° C. by the addition of 15% aqueous hydrochloric acid to a pH of 3.9 to 4.0. After the suspension has been cooled down to 2° C., it is centrifuged, washed, dried and the nicotinic acid obtained is classified by sieving. A nicotinic acid of pharmaceutical quality is obtained in a yield of 97.2% in relation to the added 3-cyanopyridine. The accumulating washing lyes are recycled. The particle distribution is between 150 and 300$\mu$ (>90%).

EXAMPLE 2

The process of example 1 is used; however, in order to free the nicotinic acid, 20% sulfuric acid is added and the suspension is cooled down to 20° C. The yield is 94.8%. The purity satisfies the pharmacopoedial requirements. The particle spectrum is between 150 and 300$\mu$ (>90%).

EXAMPLE 3

The process of example 1 is used; however, instead of sodium hydroxide solution, 5.39 kg of a 30% potassium hydroxide solution is added hourly and the precipitation is performed analogous to example 2 with sulfuric acid. The yield is 93.6%. The purity satisfies the pharmacopoedia. The particle spectrum is between 150 and 300$\mu$ (>90%).

The entire disclosure of German priority application P No. 3644049.8 is hereby incorporated by reference.

We claim:

1. A method of producing coarse-crystalline nicotinic acid with a high degree of purity comprising the steps of:
    (a) reacting an aqueous solution of 3-cyanopyridine with an equimolar amount of an alkali hydroxide dissolved in water, at a temperature between 130° and 190° C. and pressure between 1.5 and 2.0 MPa,
    (b) separating out the ammonia released during the reaction,
    (c) slowly treating the ammonia-free alkali nicotinate solution obtained at a temperature between 99° and 130° C. with an aqueous mineral acid in such a manner that the pH of the solution remains above 3.7,
    (d) subsequently cooling the developing nicotinic acid suspension down to 0° to 20° C.
    (e) separating out the crystallized nicotinic acid whereby crystals having a particle distribution of between 150 and 300$\mu$(>75%) are formed.
2. A method according to claim 1, wherein 10 to 25% by weight hydrochloric acid is used as the mineral acid.
3. A method according to claim 1, wherein 15 to 25% by weight sulfuric acid is used as the mineral acid.
4. A method according to claim 1, wherein the mineral acid is added to the solution until a pH of 3.9 to 4.1 is obtained.
5. A method according to claim 2, wherein the mineral acid is added to the solution until a pH of 3.9 to 4.1 is obtained.
6. A method according to claim 3, wherein the mineral acid is added to the solution until a pH of 3.9 to 4.1 is obtained.
7. A method according to claim 4, wherein the alkali hydroxide is sodium hydroxide or potassium hydroxide and the mineral acid is hydrochloric acid or sulfuric acid.

* * * * *